United States Patent
Nam et al.

(10) Patent No.: US 10,662,296 B2
(45) Date of Patent: May 26, 2020

(54) SUPER ABSORBENT POLYMER GRANULES AND PREPARATION METHOD THEREOF

(71) Applicant: LG Chem, Ltd., Seoul (KR)

(72) Inventors: Dae Woo Nam, Daejeon (KR); Kyung Moo Lee, Daejeon (KR); Jae Hong Lee, Daejeon (KR); Chang Sun Han, Daejeon (KR)

(73) Assignee: LG Chem, Ltd. (KR)

( * ) Notice: Subject to any disclaimer, the term of this patent is extended or adjusted under 35 U.S.C. 154(b) by 217 days.

(21) Appl. No.: 15/751,049

(22) PCT Filed: Sep. 27, 2016

(86) PCT No.: PCT/KR2016/010823
§ 371 (c)(1),
(2) Date: Feb. 7, 2018

(87) PCT Pub. No.: WO2017/065426
PCT Pub. Date: Apr. 20, 2017

(65) Prior Publication Data
US 2018/0237593 A1    Aug. 23, 2018

(30) Foreign Application Priority Data

Oct. 14, 2015  (KR) .................... 10-2015-0143415

(51) Int. Cl.
| C08J 3/24 | (2006.01) |
| C08J 3/075 | (2006.01) |
| C08J 3/12 | (2006.01) |
| A61L 15/60 | (2006.01) |
| C08K 3/36 | (2006.01) |

(52) U.S. Cl.
CPC ............ *C08J 3/075* (2013.01); *A61L 15/60* (2013.01); *C08J 3/12* (2013.01); *C08J 3/24* (2013.01); *C08K 3/36* (2013.01); *C08J 2357/10* (2013.01); *C08K 2201/005* (2013.01)

(58) Field of Classification Search
CPC ... C08J 3/075; C08J 3/24; A61L 15/60; C08K 3/36; C08K 2201/055
See application file for complete search history.

(56) References Cited

U.S. PATENT DOCUMENTS

| 4,446,261 A | 5/1984 | Yamasaki et al. |
| 4,500,670 A | 2/1985 | McKinley et al. |
| 4,732,968 A | 3/1988 | Obayashi et al. |
| 6,228,930 B1 | 5/2001 | Dairoku et al. |
| 2004/0214946 A1 | 10/2004 | Smith et al. |
| 2004/0249120 A1 | 12/2004 | Nagasawa et al. |
| 2005/0113252 A1 | 5/2005 | Miyake et al. |
| 2006/0247351 A1 | 11/2006 | Torii et al. |
| 2010/0028568 A1 | 2/2010 | Weaver et al. |
| 2010/0261812 A1 | 10/2010 | Qin et al. |
| 2011/0003926 A1 | 1/2011 | Nogi et al. |
| 2014/0051813 A1 | 2/2014 | Won et al. |
| 2015/0087742 A1 | 3/2015 | Won et al. |
| 2015/0259522 A1 | 9/2015 | Lee et al. |
| 2016/0288088 A1 | 10/2016 | Kim et al. |
| 2017/0266641 A1 | 9/2017 | Kim et al. |

FOREIGN PATENT DOCUMENTS

| CN | 1636629 A | 7/2005 |
| CN | 1847289 A | 10/2006 |
| CN | 101142259 A | 3/2008 |
| CN | 104144973 A | 11/2014 |
| CN | 104334614 A | 2/2015 |
| EP | 0450922 | 10/1991 |
| JP | S56161408 A | 12/1981 |
| JP | S57158209 A | 9/1982 |
| JP | S57198714 A | 12/1982 |
| JP | H0770328 A | 3/1995 |
| JP | H08113653 A | 5/1996 |
| JP | H10204184 A | 8/1998 |
| JP | 2005097604 A | 4/2005 |

(Continued)

OTHER PUBLICATIONS

International Search Report for Application No. PCT/KR2016/010823, dated Jan. 6, 2017.
Odian, G.G., Principles of Polymerization, Second Edition, A Wiley-Interscience Publication, Oct. 1981, p. 203.
Schwalm, R., UV Coatings; Basics, Recent Developments and New Applications, Elsevier Science, Dec. 21, 2006, p. 115.
Bucholz et al., "Modern Superabsorbent Polymer Technology", Wiley-VCH, 1998, pp. 69-103, Fig.3.1.
Third Party Observation for Application No. EP16855643.9 dated Apr. 20, 2018.
Third Party Observation for Application No. PCT/KR2016/010823 dated Feb. 9, 2018.

(Continued)

*Primary Examiner* — Kara B Boyle
(74) *Attorney, Agent, or Firm* — Lerner, David, Littenberg, Krumholz & Mentlik, LLP

(57) ABSTRACT

The present disclosure relates to a preparation method of super absorbent polymer granules and super absorbent polymer granules prepared according to the same. More specifically, the preparation method of the present disclosure includes the steps of: forming a hydrogel polymer by carrying out a thermal polymerization or a photopolymerization of a monomer composition including a water-soluble ethylene-based unsaturated monomer and a polymerization initiator; drying and pulverizing the hydrogel polymer; classifying the pulverized polymer into a first fine powder having a particle size of 150 μm or less, and a base resin having a particle size of 150 μm or more and 850 μm or less; surface-crosslinking the base resin; classifying the surface crosslinked base resin to separate a second fine powder having a particle size of 150 μm or less; and forming fine powder granules by mixing the first fine powder, the second fine powder, and silica in a wet state.

9 Claims, 1 Drawing Sheet

(56) References Cited

FOREIGN PATENT DOCUMENTS

| JP | 5524042 B2 | 6/2014 | |
|----|-----|-----|-----|
| KR | 20120047035 A * | 5/2012 | ............. B01J 20/26 |
| KR | 20120047035 A | 5/2012 | |
| KR | 20120059169 A | 6/2012 | |
| KR | 20120059169 A * | 6/2012 | ................ C08J 7/12 |
| KR | 20140036866 A | 3/2014 | |
| KR | 20140063457 A * | 5/2014 | .......... B01J 20/3021 |
| KR | 20140063457 A | 5/2014 | |
| KR | 20140145810 A | 12/2014 | |
| KR | 20140145810 A * | 12/2014 | ............. B01J 20/26 |
| KR | 101507287 B1 | 3/2015 | |
| KR | 101527585 B1 | 6/2015 | |
| KR | 20150066454 A | 6/2015 | |
| KR | 101632058 B1 | 6/2016 | |
| KR | 20160084041 A | 7/2016 | |
| KR | 20160085017 A | 7/2016 | |
| WO | 9511932 A1 | 5/1995 | |
| WO | 2009028568 A1 | 3/2009 | |

OTHER PUBLICATIONS

Chinese Search Report for Application No. CN 201680047609.1 dated Mar. 18, 2020, 2 pages.

\* cited by examiner

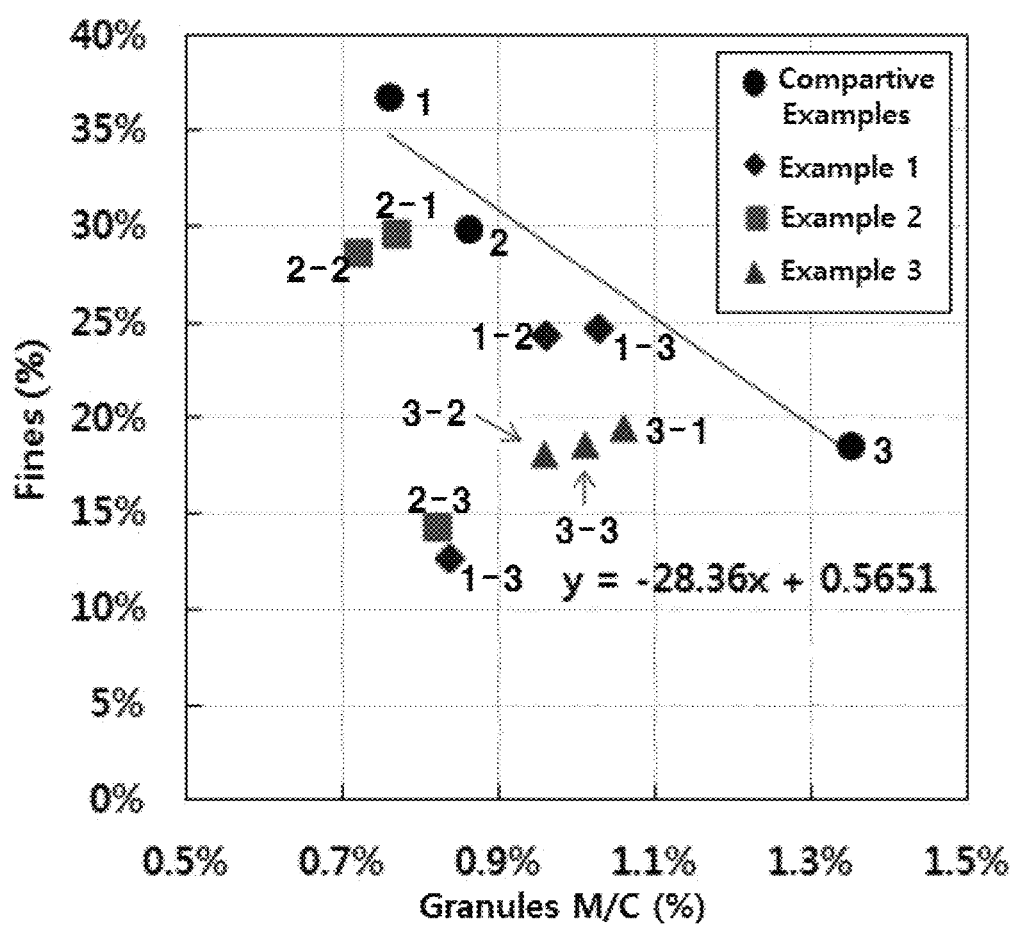

SUPER ABSORBENT POLYMER GRANULES AND PREPARATION METHOD THEREOF

CROSS-REFERENCE TO RELATED APPLICATIONS

This application is a national phase entry under 35 U.S.C. § 371 of International Application No. PCT/KR2016/010823, filed Sep. 27, 2016, which claims priority to Korean Patent Application No. 10-2015-0143415, filed Oct. 14, 2015, the disclosures of which are incorporated herein by reference.

BACKGROUND OF THE INVENTION

(a) Field of the Invention

The present disclosure relates to super absorbent polymer granules having a high fine powder aggregation strength and gel strength, and the preparation method of the same.

(b) Description of the Related Art

A super absorbent polymer (SAP) is a type of synthetic polymeric material capable of absorbing 500 to 1000 times its own weight of moisture. Various manufacturers have denominated it with different names, such as SAM (Super Absorbency Material), AGM (Absorbent Gel Material), and the like. Such super absorbent polymers started to be practically applied in sanitary products, and they are now being widely used not only for hygiene products such as disposable diapers for children, etc., but also for water retaining soil products for gardening, water stop materials for the civil engineering and construction, sheets for raising seedling, fresh-keeping agents for food distribution fields, materials for poultices, or the like.

As a preparation method of such super absorbent polymers, a method of reverse phase suspension polymerization and a method of solution polymerization have been known. For example, Japanese Patent Laid-open Publication Nos. S56-161408, S57-158209, and S57-198714 disclose the reverse phase suspension polymerization. The method of solution polymerization further includes a thermal polymerization in which a polymerization gel is polymerized while being broken and cooled in a kneader equipped with a plurality of shafts, and a photo-polymerization in which an aqueous solution at a high concentration is irradiated with UV rays onto a belt to be polymerized and dried at the same time.

The hydrogel polymer obtained through the polymerization reaction is generally marketed as a powdered product after it is dried and pulverized.

At this time, fine powders (fines) having a particle diameter of about 150 µm or less may be formed during the steps of cutting, pulverizing and powdering the dried polymer. It is considered undesirable to apply the super absorbent polymer particle including the fine powder to hygiene goods such as a baby diapers and an adult urinary incontinence device because it may be moved before being used or may show decreased physical properties.

Therefore, the process for excluding the fine powders so that the fine powder is not included in a final product or the regranulating process for aggregating the fine powders to be normal particle size is needed. However, the reassembled polymer may be easily re-broken into the fine powders, since its aggregation strength and gel strength are low.

Accordingly, it is still necessary to develop a preparation method of super absorbent polymer granules that can have a high fine powder aggregation strength and gel strength to reduce the production of fine powders from the reassembled polymer.

PRIOR ART LITERATURE

Patent Literature (PATENT LITERATURE 1) Japanese Patent Laid-open Publication No. S56-161408
(PATENT LITERATURE 2) Japanese Patent Laid-open Publication No. S57-158209
(PATENT LITERATURE 3) Japanese Patent Laid-open Publication No. S57-198714

DETAILED DESCRIPTION OF THE INVENTION

Technical Problem

The present disclosure is to provide super absorbent polymer granules having a high fine powder aggregation strength and gel strength, and the preparation method of the same.

Technical Solution

The present disclosure provides a preparation method of super absorbent polymer granules, including the steps of:

forming a hydrogel polymer by carrying out a thermal polymerization or a photopolymerization of a monomer composition including a water-soluble ethylene-based unsaturated monomer and a polymerization initiator;

drying and pulverizing the hydrogel polymer;

classifying the pulverized polymer into a first fine powder having a particle size of 150 µm or less, and a base resin having a particle size of 150 µm or more and 850 µm or less;

surface-crosslinking the base resin;

classifying the surface crosslinked base resin to separate a second fine powder having a particle size of 1.50 µm or less; and forming fine powder granules by mixing the first fine powder, the second fine powder, and silica in a wet state.

In addition, the present disclosure provides super absorbent polymer granules, which satisfy a relationship of $y \leq -28.36x + 0.5651$, wherein x is the moisture content (%), and y is the content of the fine powder (%).

Hereinafter, the preparation method of super absorbent polymer granules and the super absorbent polymer granules according to the exemplary embodiments of the present disclosure will be described in more detail.

Prior to that, the terms including ordinal numbers such as "first" and "second" are used to describe various components, but the components are not limited by the terms. The terms are used to distinguish one component from another component.

According to an embodiment of the present disclosure, a preparation method of super absorbent polymer granules is provided, the method including the steps of:

forming a hydrogel polymer by carrying out a thermal polymerization or a photopolymerization of a monomer composition including a water-soluble ethylene-based unsaturated monomer and a polymerization initiator;

drying and pulverizing the hydrogel polymer;

classifying the pulverized polymer into a first fine powder having a particle size of 150 μm or less, and a base resin having a particle size of 150 μm or more and 850 μm or less;

surface-crosslinking the base resin;

classifying the surface crosslinked base resin to separate a second fine powder having a particle size of 150 μm or less; and forming fine powder granules by mixing the first fine powder, the second fine powder, and silica in a wet state.

In the preparation method of super absorbent polymer granules, the monomer composition, the raw material of the super absorbent polymer, includes a water-soluble ethylene-based unsaturated monomer and a polymerization initiator.

As the water-soluble ethylene-based unsaturated monomer, any monomer that is generally used in the preparation of the super absorbent polymer may be used without limitation.

For example, one or more monomers selected from the group consisting of an anionic monomer and a salt thereof, a nonionic hydrophilic monomer, and an unsaturated monomer containing amino group and a quaternary compound thereof may be used.

Specifically, one or more compounds selected from the group consisting of an anionic monomer such as (meth) acrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, and a salt thereof; a nonionic hydrophilic monomer such as (meth)acrylamide, N-substituted(meth)acrylate, 2-hydroxyethyl(meth)acrylate, 2-hydroxypropyl(meth)acrylate, methoxypolyethyleneglycol(meth)acrylate, or polyethyleneglycol(meth)acrylate; and an unsaturated monomer containing amino group such as (N,N)-dimethylaminoethyl (meth)acrylate or (N,N)-dimethylaminopropyl(meth) acrylamid, and a quaternary compound thereof may be used.

More preferably, acrylic acid or salts thereof, for example, acrylic acid or alkali metal salts thereof such as sodium salts, may be used. By using such monomer, it becomes possible to prepare a super absorbent polymer having superior physical properties. When the alkali metal salt of acrylic acid is used as the monomer, it is possible to use acrylic acid after neutralizing the same with a basic compound such as sodium hydroxide (NaOH).

The concentration of the water-soluble ethylene-based unsaturated monomer may be about 20 to about 60 wt %, preferably about 40 to about 50 wt %, based on the monomer composition including the raw materials of the super absorbent polymer and the solvent, and it may be controlled to be an adequate concentration in consideration of the polymerization time and the reaction conditions. However, if the concentration of the monomer is excessively low, the yield of the super absorbent polymer is low and there may be a problem in economic efficiency. In contrast, if the concentration is excessively high, it may cause problems in processes that some of the monomer may be extracted or the pulverization efficiency of the prepared hydrogel polymer may be lowered in the pulverizing process, and thus the physical properties of the super absorbent polymer may be deteriorated.

In addition, the polymerization initiator is not particularly limited, as long as it is generally used in the preparation of the super absorbent polymer. It may be a thermal polymerization initiator or a photopolymerization initiator by UV irradiation, depending on a polymerization method. However, even in the case of using the photopolymerization method, because a certain amount of heat is generated by the ultraviolet irradiation or the like and a certain amount of heat is also generated according to the progress of the polymerization reaction which is exothermic, a thermal polymerization initiator may be additionally included.

The photopolymerization initiator can be used without any limitation as long as it is a compound capable of forming radicals by a light such as an UV ray.

As the photopolymerization initiator, for example, one or more selected from the group consisting of benzoin ether, dialkyl acetophenone, hydroxyl alkylketone, phenyl glyoxylate, benzyl dimethyl ketal, acyl phosphine, and α-aminoketone may be used. Meanwhile, as the specific example of acyl phosphine, phenylbis(2,4,6-trimethylbenzoyl) phosphine oxide may be used. More various photopolymerization initiators are well disclosed in "UV Coatings: Basics, Recent Developments and New Application (Elsevier, 2007)" written by Reinhold Schwalm, p 115, however, they are not limited to the above described examples.

The concentration of the photopolymerization initiator may be about 0.01 to about 1.0 wt %, based on the monomer composition. If the concentration of the photopolymerization initiator is too low, the polymerization rate may become low. If the concentration of the photopolymerization initiator is too high, the molecular weight of the super absorbent polymer may become low and its physical properties may not be uniform.

Also, as the thermal polymerization initiator, one or more initiators selected from the group consisting of a persulfate-based initiator, an azo-based initiator, hydrogen peroxide, and ascorbic acid may be used. Specific examples of the persulfate-based initiator may include sodium persulfate ($Na_2S_2O_8$), potassium persulfate ($K_2S_2O_8$), ammonium persulfate (($NH_4$)$_2S_2O_8$), and the like; and examples of the azo-based initiator may include 2,2-azobis-(2-amidinopropane)dihydrochloride, 2,2-azobis-(N,N-dimethylene)isobutyramidine dihydrochloride, 2-(carbamoylazo)isobutylonitrile, 2,2-azobis[2-(2-imidazolin-2-yl)propane] dihydrochloride, 4,4-azobis-(4-cyanovaleric acid) and the like. More various thermal polymerization initiators are well disclosed in "Principle of Polymerization (Wiley, 1981)" written by Odian, p 203, however, they are not limited to the above described examples.

The concentration of the thermal polymerization initiator may be about 0.001 to about 0.5 wt %, based on the monomer composition. If the concentration of the thermal polymerization initiator is too low, additional thermal polymerization hardly occurs, and thus the addition effect of the thermal polymerization initiator may not be sufficient. If the concentration of the thermal polymerization initiator is too high, the molecular weight of the super absorbent polymer may become low and its physical properties may not be uniform.

In addition, the monomer composition may further include an internal crosslinking agent as a raw material of the super absorbent polymer. The internal crosslinking agent may be a crosslinking agent having one or more ethylene-based unsaturated groups in addition to the functional group which may react with the water-soluble substituents of the water-soluble ethylene-based unsaturated monomer; or a crosslinking agent having two or more functional groups which may react with the water-soluble substituents of the monomer and/or the water-soluble substituents formed by hydrolysis of the monomer.

As the specific example of the internal crosslinking agent, a C8-C12 bisacrylamide, bismethacrylamide, a poly(meth) acrylate of C2-C10 polyol, a poly(meth)alkylether of C2-C10 polyol, or the like may be used. More specifically, one or more agents selected from the group consisting of N,N'-methylenebis(meth)acrylate, ethyleneoxy(meth)acrylate, polyethyleneoxy(meth)acrylate, propyleneoxy(meth) acrylate, glycerin diacrylate, glycerin triacrylate, trimethylol triacrylate, triallylamine, triarylcyanurate, triallylisocyanate, polyethyleneglycol, diethyleneglycol, and propyleneglycol may be used.

Such internal crosslinking agent may be included in an amount of about 0.01 to about 0.5 wt %, based on the monomer composition, and it may crosslink the polymerized polymer.

In addition, the monomer composition of the preparation method of super absorbent polymer granules of the embodiment may further include additives such as a thickener, a plasticizer, a storage stabilizer, an antioxidant, and the like, as needed.

The raw materials such as the water-soluble ethylene-based unsaturated monomer, the photopolymerization initiator, the thermal polymerization initiator, the internal crosslinking agent, and the additives may be prepared in the form of the monomer composition solution which is dissolved in a solvent.

In this regard, the solvent can be used without any limitation as long as it can dissolve the above-described components. For example, one or more solvents selected from the group consisting of water, ethanol, ethylene glycol, diethylene glycol, triethylene glycol, 1,4-butanediol, propylene glycol, ethylene glycol monobutylether, propylene glycol monomethylether, propylene glycol monomethylether acetate, methylethylketone, acetone, methylamylketone, cyclohexanone, cyclopentanone, diethylene glycol monomethylether, diethyleneglycol ethylether, toluene, xylene, butylolactone, carbitol, methylcellosolve acetate, N,N-dimethyl acetamide, and the like may be used alone or in combination with each other.

The solvent may be included in the monomer composition in a residual quantity excluding the above-described components.

Meanwhile, the method for forming a hydrogel polymer by the thermal polymerization or photopolymerization of the monomer composition is not particularly limited as long as it is a method typically used in the art.

Specifically, the polymerization method is largely classified into a thermal polymerization and a photopolymerization depending on energy source of the polymerization. The thermal polymerization may be typically carried out in a reactor like a kneader equipped with agitating spindles, and the photopolymerization may be carried out in a reactor equipped with a movable conveyor belt. However the above-described polymerization method is an example only, and the present disclosure is not limited thereto.

For example, as described above, a hydrogel polymer may be obtained by thermal polymerization through supplying hot air to a reactor like a kneader equipped with the agitating spindles or by heating the reactor. At this time, the hydrogel polymer may have a size of centimeters or millimeters when it is discharged from the outlet of the reactor, depending on the type of the agitating spindles equipped in the reactor. Specifically, the size of the hydrogel polymer may vary depending on the concentration of the monomer composition injected thereto, the injection rate or the like, and the hydrogel polymer having a weight average particle diameter of 2 to 50 mm can be generally obtained.

Furthermore, when the photopolymerization is carried out in a reactor equipped with a movable conveyor belt, the form of the hydrogel polymer obtained may be usually a sheet-type hydrogel polymer having a width of the belt. In this case, the thickness of the polymer sheet may vary depending on the concentration of the monomer composition fed thereto and the feeding speed, and the feeding speed of the monomer composition is preferably controlled so that the polymer sheet having a thickness of about 0.5 to about 5 cm is obtained. If the monomer composition is fed so that the thickness of the sheet-type polymer becomes too thin, the production efficiency becomes low, which is not preferred. If the thickness of the sheet-type polymer exceeds 5 cm, the polymerization reaction may not uniformly occur throughout the whole thickness due to its excessively thick thickness.

The hydrogel polymer obtained by such method may have typically a moisture content of about 40 to about 80 wt %. Meanwhile, the term "moisture content" as used herein refers to the content of moisture in the total weight of the hydrogel polymer, which is obtained by subtracting the weight of the dried polymer from the weight of the hydrogel polymer. Specifically, it is defined as a value calculated by measuring the weight loss according to evaporation of water in the polymer during the drying process by increasing the temperature of the polymer through infrared heating. In this case, the moisture content of the hydrogel polymer is measured by using MX-50 manufactured by AND Co. and 5 g of sample, and setting the condition at 180° C. for 40 minutes.

Subsequently, a step of drying the hydrogel polymer thus obtained is carried out.

In this case, in order to increase the efficiency of the drying step, a coarsely pulverizing step may be further carried out before drying, as needed.

A pulverizing device used herein may include, but its configuration is not limited to, for example, any one selected from the group consisting of a vertical pulverizer, a turbo cutter, a turbo grinder, a rotary cutter mill, a cutter null, a disc mill, a shred crusher, a crusher, a chopper, and a disc cutter. However, it is not limited thereto.

In addition, the pulverizing step may be carried out so that the particle size of the hydrogel polymer becomes about 2 to about 10 mm. Pulverizing the hydrogel polymer into a particle size of less than 2 mm is technically not easy due to its high moisture content, and agglomeration may occur between the pulverized particles. Meanwhile, if the polymer is pulverized into a particle size of greater than 10 mm, the effect of increasing the efficiency in the subsequent drying step may be insignificant.

The hydrogel polymer pulverized as above or the hydrogel polymer immediately after polymerization without the pulverizing step is subjected to a drying step. In this case, the drying temperature of the drying step may be about 150 to about 250° C. If the drying temperature is less than 150° C., it is likely that the drying time becomes too long and the physical properties of the super absorbent polymer finally formed is deteriorated. If the drying temperature is higher than 250° C., only the surface of the polymer is dried, and thus it is likely that fine powders are generated during the subsequent pulverizing step and the physical properties of the super absorbent polymer finally formed is deteriorated. Therefore, the drying step may be preferably carried out at a temperature of about 150 to about 200° C., and more preferably at a temperature of about 160 to about 190° C.

Meanwhile, the drying time may be about 20 to about 90 minutes, in consideration of the process efficiency, but it is not limited thereto.

The drying method may also be selected and used without any limitation, as long as it is a method generally used for drying the hydrogel polymer. Specifically, the drying step may be carried out by a method such as hot air supply, infrared irradiation, microwave irradiation or ultraviolet irradiation. When the drying step as above is finished, the moisture content of the polymer may be about 0.1 to about 10 wt %.

Subsequently, the dried polymer obtained from the drying step is subjected to a pulverization step.

The polymer powder obtained after the pulverizing step may have a particle size of about 850 µm or less. Specific examples of a pulverizing device that can be used to achieve the above particle size may include a pin mill, a hammer mill, a screw mill, a roll mill, a disc mill, a jog mill or the like, but the present disclosure is not limited thereto.

Also, the pulverized polymer is classified into a first fine powder having a particle size of 150 µm or less, and a base resin having a particle size of 150 µm or more and 850 µm or less. That is, the classifying step may include the step of classifying the pulverized hydrogel polymer into two kinds of particles: particles having a particle size of 150 µm or less and particles having a particle size of 150 µm or more and 850 µm or less.

In the present disclosure, a fine particle having a particular particle size or less, that is, a particle size of about 150 µm or less, is referred to as a super absorbent polymer fine powder, a polymer fine powder, SAP fines or a fine powder. The fine powder may be generated during the polymerization step, the drying step or the pulverizing step of the dried polymer. However, when the fine powder is included in a product, handling is difficult and it may show a phenomenon of gel blocking and deteriorate the physical properties. Therefore, it is preferable to exclude the fine powder or reassemble the fine powder to be a normal particle so that it is not included in a final resin product.

The first fine powder is obtained by drying and pulverizing the hydrogel polymer, and separating the same by classification. Therefore, as will be described later, it is distinguished from the second fine powder which is separated by classifying the base resin after surface treatment.

Subsequently, the base resin having a particle size of 150 µm or more and 850 µm or less separated from the classifying step is subjected to a surface-crosslinking step. The surface crosslinking is a process of increasing the crosslinking density in the vicinity of the surface of the super absorbent polymer particle with regard to the crosslinking density inside the particle. In general, the surface crosslinking agent is applied to the surface of the super absorbent polymer particle. Therefore, this reaction occurs on the surface of the super absorbent polymer particle, which improves crosslinking on the surface of the particle without substantially affecting the inside of the particle. Thus, the surface-crosslinked super absorbent polymer particles have a higher level of crosslinking in the vicinity of the surface than in the inside.

In this case, the surface crosslinking agent is not particularly limited as long as it is a compound capable of reacting with functional groups of the polymer.

Preferably, in order to improve the properties of the prepared super absorbent polymer, one or more selected from the group consisting of a polyhydric alcohol compound; an epoxy compound; a polyamine compound; a haloepoxy compound; a condensation product of the haloepoxy compound; an oxazoline compound; a mono-, di- or polyoxazolidinone compound; a cyclic urea compound; a polyvalent metal salt; and an alkylene carbonate compound may be used as the surface crosslinking agent.

Specific examples of the polyhydric alcohol compound may include one or more selected from the group consisting of mono-, di-, tri-, tetra- or polyethylene glycol, monopropylene glycol, 1,3-propanediol, dipropylene glycol, 2,3,4-trimethyl-1,3-pentanediol, polypropylene glycol, glycerol, polyglycerol, 2-butene-1,4-diol, 1,4-butanediol, 1,3-butanediol, 1,5-pentanediol, 1,6-hexanediol, and 1,2-cyclohexane dimethanol.

Further, the epoxy compound may include ethylene glycol diglycidyl ether, glycidol and the like. The polyamine compound may include one or more selected from the group consisting of ethylene diamine, diethylene triamine, triethylene tetraamine, tetraethylene pentamine, pentaethylene hexamine, polyethylene imine, and polyamide polyamine.

Further, the haloepoxy compound may include epichlorohydrin, epibromohydrin, or α-methylephichlorohydrin. Meanwhile, the mono-, di-, or polyoxazolidinone compound may include, for example, 2-oxazolidinone and the like.

Further, the alkylene carbonate compound may include ethylene carbonate, propylene carbonate and the like. These may be used alone or in combination with each other. On the other hand, to increase the efficiency of the surface crosslinking process, one or more of polyhydric alcohols may be preferably included among these surface crosslinking agents. More preferably, polyhydric alcohol compounds having 2 to 10 carbon atoms may be used.

The amount of the surface crosslinking agent added may be appropriately selected depending on the kind of the surface crosslinking agent added or the reaction conditions. However, the surface crosslinking agent may be generally used in an amount of about 0.001 to about 5 parts by weight, preferably about 0.01 to about 3 parts by weight, and more preferably about 0.05 to about 2 parts by weight, based on 100 parts by weight of the polymer.

If the amount of the surface crosslinking agent is excessively small, the surface crosslinking reaction hardly occurs, and if the amount is higher than 5 parts by weight based on 100 parts by weight of the polymer, the absorptivity and the physical properties may be decreased due to excessive surface crosslinking reaction.

The crosslinking reaction and the drying process may be carried out simultaneously by heating the polymer particles to which the surface crosslinking agent is added.

The temperature elevating means for the surface crosslinking reaction is not particularly limited, and may include applying a heat transfer medium or directly applying a heat source. In this case, examples of the heat transfer medium used herein may include, but are not limited thereto, any heated fluid, such as steam, hot air, or hot oil. And, the temperature of the heat transfer medium may be property selected in consideration of the means for the heat transfer medium, the heating rate, and the desired heating temperature. Examples of the heat source directly provided may include, but are not limited to, an electric heater or a gas heater.

Subsequently, the surface crosslinked base resin is subjected to a classifying step to separate a second fine powder having a particle size of 150 µm or less. After the surface crosslinking step, a general drying process may be further performed before the classifying step, and the drying methods and conditions of the hydrogel polymer described above can be applied without any limitations.

That is, the second fine powder is obtained by classifying the surface-crosslinked base resin. Therefore, it is distinguished from the first fine powder which is separated by drying and pulverizing the hydrogel polymer, and classifying the same as described above.

Subsequently, fine powder granules are formed by mixing the first fine powder, the second fine powder, and silica in a wet state.

Herein, the step of forming fine powder granules may be carried out by mixing the first fine powder, the second fine powder, and the silica with water of 50 to 90° C. to reassemble in a wet state. When the silica is used in the step of forming the powder granules, the contact area between the fine powders and the silica may be widened and the bonding strength between the particles may be increased. Therefore, the fine powder granules prepared according to the preparation method of super absorbent polymer granules of the embodiment may exhibit an excellent aggregation strength and gel strength.

In this case, the water may be contained in an amount of 50 to 150 parts by weight, preferably 70 to 130 parts by weight based on 100 parts by weight of the first fine powder and the second fine powder.

As the silica, any silica known to be used in the art may be used without limitation. For example, colloidal silica, fumed silica, silicate, and the like may be used. In addition, as the silicate, laponite, bentonite, saponite, and the like may be dispersed in water in the form of colloidal and used.

Further, the silica may have a primary particle size of 5 to 100 nm, preferably 5 to 30 nm. The primary particle size refers to an individual size before the agglomeration of the silica. When the silica having a small size in the above range is used, the contact area between the fine powders and the silica may be widened. Such silica may have a size of 10 μm or less when agglomerated.

In the step of forming fine powder granules, the silica may be contained in an amount of 0.005 to 0.5 parts by weight, preferably 0.03 to 0.15 parts by weight based on 100 parts by weight of the first fine powder and the second fine powder.

In addition, a moisture content of the first fine powder and the second fine powder may be 40 to 60% in the step of forming fine powder granules. That is, as described above, the step of forming fine powder granules is carried out by mixing the first fine powder and the second fine powder with water to reassemble in a wet state. At this time, in order to increase the aggregation strength, the regranulating may be performed after wetting the fine powder to be about 40 to about 60% of the moisture content. In this case, as the moisture content is high, the aggregation strength of the fine powder is increased. However, in the regranulating process, massive granules lumps or granules lumps (jelly balls) in a solidly aggregated state since the fine powder partially contain a large amount of moisture may occur, which may cause problems in operation of the subsequent pulverization process. In addition, when the moisture content is low, the regranulating process is easy, but the aggregation strength is low, and thus, there are many cases that the polymer is crushed again into fine powders after regranulating.

In addition, the first fine powder and the second fine powder may be mixed at a weight ratio of 10:1 to 1:1, preferably 8:2 to 9:1 in the step of forming fine powder granules. Since the fine powders before and after the surface-crosslinking treatment are mixed together and the regranulating step is carried out, there is an effect that the aggregation strength of the fine powder granules is increased, when the ratio of the fine powder after the surface-crosslinking treatment is decreased.

In the meantime, the preparation method of super absorbent polymer granules of the embodiment may further include a step of drying the fine powder granules. In this case, the drying methods and conditions of the hydrogel polymer described above can be applied without any limitations. The moisture content of the polymer after the drying step above may be about 0.1 to about 10 wt %.

In addition, after drying the fine powder granules, a step of pulverizing or classifying the dried fine powder granules may be further carried out to make the particle size about 150 to about 850 μm. The pulverizing and classifying methods and conditions of the hydrogel polymer described above can be applied without any limitations.

The fine powder granules obtained according to the preparation method may be used alone or may be applied to a product by mixing with a polymer having a normal particle size of 150 to 850 μm.

According to another embodiment of the present disclosure, super absorbent polymer granules are provided, which satisfy a relationship of y≤−28.36x+0.5651, wherein x is the moisture content (%), and y is the content of the fine powder (%). The moisture content x is a value obtained by measuring the ratio (%) of the reduced weight at 140° C. for 10 minutes by using 5 g of the whole sample of the pulverized fine powder granules and MX-50 manufactured by AND Co. The content of the fine powder y is a value obtained by measuring the wt % of the particles having passed through 100 mesh after pulverizing the fine powder granules for 15 seconds using a hood mixer (HMF-3260S, Hanil Electric Co., Ltd.) with a crushing strength of "weak" and classifying the same, i.e., the particles having a particle size of 150 μm or less.

The super absorbent polymer granules satisfying this relationship are characterized in that the content of the fine powder is low relative to the moisture content, so that the generation of fine powder is decreased at the same moisture content, as the silica is used in the step of forming the fine powder granules.

The relationship of the moisture content (%) x and the content of the fine powder (%) y may be derived by plotting the moisture content on the x-axis and the content of the fine powder on the y-axis, and then linear regression of the same. An example of the relationship of x and y is illustrated in FIG. 1.

In addition, the fine powder granules prepared according to the preparation method of super absorbent polymer granules of the embodiment may have a fine powder content of less than about 30%, when the moisture content is in the range of about 0.3 to 1.2%.

Further, the fine powder granules prepared according to the preparation method of the embodiment may have a gel strength of 8,500 Pa or more, preferably 8,700 to 15,000 Pa, as measured using a rheometer.

The gel strength is measured by the following method for 5 minutes and then taken as an average value. More specifically, 0.5 g of the fine powder granules formed by the above-described method are taken after sieving through a 30-50 Mesh (300-600 μm) sieve, and are swollen sufficiently in 50 g of 0.9% NaCl solution for 1 hour. Thereafter, a swollen gel was spread on a Buchner funnel covered with a filter paper (Whatman, 1004-110 Model, pore size of 20-25 μm), and the remaining fluid was removed by vacuum for 3 minutes. The gel is kept in an airtight container until the test is ready.

Then, before the gel is placed between the rheometer and a parallel plate, it is sucked into the filter paper so that there is no residual water between the particles during testing.

2 g of the swollen gel is measured using a rheometer, and the test conditions of the rheometer are: Plate Gap Size 2 mm; Strain amplitude 1%; Oscilation frequency 10 radian/sec; ambient temperature 22° C.; plate 25 mm, TA Instruments—AR Series.

In addition, the super absorbent polymer granules satisfying the relationship of the moisture content (%) and the content of the fine powder (%) may be prepared according to the preparation method of super absorbent polymer granules of the embodiment. More specifically, the fine powder granules prepared according to the preparation method have a high aggregation strength even after the drying and pulverizing step, thus show a low rate of re-crushing into fine powders, since the silica is used in the step of forming the fine powder granules.

According to the preparation method of super absorbent polymer granules of the present disclosure, it is possible to provide a super absorbent resin having a high fine powder aggregation strength and gel strength.

BRIEF DESCRIPTION OF THE DRAWINGS

FIG. 1 is a graph showing the relationship between the moisture content and the content of the fine powder of the fine powder granules prepared in Examples and Comparative Examples.

DETAILED DESCRIPTION OF THE EMBODIMENT

Hereinafter, the preparation method of super absorbent polymer granules and the super absorbent polymer granules according to the exemplary embodiments of the present disclosure will be described in more detail.

PREPARATION EXAMPLE 100 g of acrylic acid, 0.5 g of polyethylene glycol diacrylate (Mw=523) as a crosslinking agent, 0.2 g of sodium persulfate as a thermal initiator, 0.008 g of phenylbis (2,4,6-trimethylbenzoyl) phosphine oxide as a UV initiator, 40 g of NaOH, and 127 g of water were mixed to prepare a monomer aqueous solution composition having a monomer concentration of 45.8 wt %.

The monomer aqueous solution composition was introduced into a feeder of a polymerization reactor equipped with a continuous conveyer belt. And then, the composition was irradiated with ultraviolet rays (irradiation amount: 15 mW/cm$^2$) by a UV irradiation apparatus while maintaining the polymerization atmosphere temperature at 80° C., and UV polymerization was carried out for 2 minutes to prepare a hydrogel polymer.

The hydrogel polymer was transferred to a meat chopper and then cut to 0.1~0.2 cm. At this time, the moisture content of the hydrogel polymer which was cut was 47 wt %.

Then, the hydrogel polymer was dried in a hot-air dryer at a temperature of 170° C. and an air flow rate of 0.8 m/sec for 30 minutes, and the dried hydrogel polymer was pulverized with a pin mill. Then, a polymer having a particle size (average particle diameter size) of 150 μm or less and a polymer having a particle size of 150 μm to 850 μm were classified using a sieve. A base resin was prepared through this process. In order to reassemble the fine powder having a particle size of 150 μm or less generated in the above process, it was separately classified and managed as a first fine powder.

Thereafter, the base resin and a surface-crosslinking solution (0.4 wt % of ethylene carbonate, 3.5 wt % of water) were uniformly mixed, and then the classified hydrogel polymer was introduced to a surface-crosslinking reactor. And, the surface-crosslinking reaction of the hydrogel polymer was carried out at a temperature of 180° C. or higher for 40 to 60 minutes.

After the surface-crosslinking treatment, a surface-treated super absorbent resin having an average particle size of 150 to 850 μm was obtained by using a sieve with respect to the hydrogel polymer. In addition, the content of the fine powder of 150 μm or less in each of the above super absorbent resins was less than 2%. In order to reassemble the fine powder having a particle size of 150 μm or less generated in the above process, it was separately classified and managed as a second fine powder.

EXAMPLES 1800 g of the first fine powder and 200 g of the second fine powder separated in the above Preparation Example were placed in a 40 L planetary mixer (PM-040, DNTEK Co., Ltd.), and the silica shown in the following Table 1 was measured and introduced thereto. Aerosil 200 was a fumed silica of Evonik Degussa, DM-30S was a silica of Tokuyama Corporation, and SnowTex O was a colloidal silica of Nissan Chemical. Then, after closing the lid of the mixer, pressed the start button of the mixer, set the impeller rpm to 60, and set the rpm to 0 again after 60 seconds. Then, water heated to 80° C. was added to the mixer. After 60 seconds from the addition, pressed the stop button to end the mixing. Then, the fine powder granules were taken out from the mixer, placed in a tray that the bottom and side surfaces are made of stainless steel mesh, and then dried in a convection oven at 180° C. for 3 hours. Thereafter, 250 g of the dried granules were put into a hood mixer (HMF-3260S) manufactured by Hanil Electric Co., Ltd., and pulverized twice for 15 seconds with a crushing strength of "weak". Then, 500 g of the fine powder granules were classified on a sieve having a scale of 25, 30, 50, 80 and 100 mesh using a classifying apparatus (AS200, Retsch). After weighing the weights of the classified fine powder granules for each mesh, the wt % of the fine powder granules for each mesh relative to the total weight of the fine powder granules was calculated.

TABLE 1

|  | Silica | Amount of input[1] (phr) |
| --- | --- | --- |
| Example 1-1 | Aerosil 200 | 0.038 |
| Example 1-2 | Aerosil 200 | 0.076 |
| Example 1-3 | Aerosil 200 | 0.076 |
| Example 2-1 | SnowTex O | 0.038 |
| Example 2-2 | SnowTex O | 0.076 |
| Example 2-3 | SnowTex O | 0.076 |
| Example 3-1 | DM-30S | 0.038 |
| Example 3-2 | DM-30S | 0.076 |
| Example 3-3 | DM-30S | 0.076 |
| Comparative Example 1 | — | — |
| Comparative Example 2 | — | — |
| Comparative Example 3 | — | — |

*Amount of input[1] (phr): an amount to be added to 100 parts by weight of the first fine powder and the second fine powder

EXPERIMENTAL EXAMPLES (1) Fines[2] (%) under #100: It refers to the wt % of the particles (fine powder) that have passed through 100 mesh after classifying the fine powder granules.

(2) CRC (Centrifugal Retention Capacity)[3]: CRC was measured in accordance with EDANA method WSP 241.2 using 0.1 g of the particles between mesh #30-50 among the pulverized and classified granules.

Specifically, W (g) (about 0.1 g) of resin obtained from the Examples and Comparative Examples were uniformly placed into a non-woven bag, sealed, and then immersed in a saline solution (0.9 wt %) at room temperature for 30 minutes. After 30 minutes, residual water was drained by centrifugal device under the condition of 250 G for 3 minutes, and the weight $W_2$ (g) of the bag was measured. In addition, the same manipulation was performed without super absorbent polymer, and the weight $W_1$ (g) of the bag was measured. CRC (g/g) was calculated using the weights measured above by following equation.

$$CRC\ (g/g) = \{(W_2\ (g) - W_1\ (g))/W\ (g)\} - 1 \qquad \text{Equation 11}$$

(3) The gel strength (Pa): The fine powder granules were measured after sieving through a 30~50 Mesh (300-600 μm) sieve, and were swollen sufficiently in 50 g of 0.9% NaCl solution for 1 hour. Thereafter, a swollen gel was spread on a Buchner funnel covered with a filter paper (Whatman, 1004-110 Model, pore size of 20-25 μm), and the remaining fluid was removed by vacuum for 3 minutes. The gel was kept in an airtight container until the test is ready.

Then, before the gel was placed between the rheometer and a parallel plate, it was sucked into the filter paper so that there was no residual water between the particles during testing.

2 g of the swollen gel was measured using a rheometer. Herein, the test conditions of the rheometer were: Plate Gap Size 2 mm; Strain amplitude 1%; Oscilation frequency 10 radian/sec; ambient temperature 22° C. plate 25 mm, TA Instruments—AR Series. It was measured for 5 minutes and then taken as an average value.

(4) The moisture content (%)[4]: It refers to the moisture content (M/C) of the granules, and was obtained by measuring the reduced % of the weight at 140° C. for 10 minutes using MX-50 manufactured by AND Co.

TABLE 2

|  | CRC[3] (g/g) | Gel Strength (Pa) | Moisture content[4] (%) | Fines[2] (%) |
|---|---|---|---|---|
| Example 1-1 | 26.1 | 8748 | 1.03 | 24.9 |
| Example 1-2 | 25.7 | 9046 | 0.96 | 24.4 |
| Example 1-3 | 25.6 | 9745 | 0.84 | 12.8 |
| Example 2-1 | 26.0 | 9824 | 0.77 | 29.7 |
| Example 2-2 | 26.1 | 9638 | 0.72 | 28.7 |
| Example 2-3 | 26.1 | 10265 | 0.82 | 14.3 |
| Example 3-1 | 25.5 | 9275 | 1.06 | 19.7 |
| Example 3-2 | 25.8 | 9046 | 0.96 | 18.2 |
| Example 3-3 | 25.6 | 10171 | 1.01 | 18.7 |
| Comparative Example 1 | 26.9 | 8251 | 0.76 | 36.8 |
| Comparative Example 2 | 26.4 | 9437 | 0.86 | 29.9 |
| Comparative Example 3 | 25.6 | 10232 | 1.35 | 18.6 |

Referring to the Tables 1 and 2, it is confirmed that the super absorbent polymer granules prepared according to the preparation method of the Examples satisfy a relationship of $y \leq -28.36x + 0.5651$, wherein x is the moisture content, and y is the content of the fine powder, and have a high gel strength more than 8500 Pa.

In contrast, the super absorbent polymer granules of the Comparative Examples prepared without using silica exhibit the higher fine powder content at the moisture content similar to that of the Examples, and thus cannot satisfy the relationship of $y \leq -28.36x + 0.5651$, and have a lower gel strength compared with the Examples.

What is claimed is:

1. A preparation method of super absorbent polymer granules, comprising the steps of:
   forming a hydrogel polymer by carrying out a thermal polymerization or a photopolymerization of a monomer composition including a water-soluble ethylene-based unsaturated monomer and a polymerization initiator;
   drying and pulverizing the hydrogel polymer;
   classifying the pulverized polymer into a first fine powder having a particle size of 150 μm or less, and a base resin having a particle size of 150 μm or more and 850 μm or less;
   surface-crosslinking the base resin;
   classifying the surface crosslinked base resin to separate a second fine powder having a particle size of 150 μm or less; and
   forming fine powder granules by mixing the first fine powder, the second fine powder, and silica in a wet state.

2. The preparation method of claim 1, wherein the step of forming fine powder granules is carried out by mixing the first fine powder, the second fine powder, and the silica with water of 50 to 90° C. to reassemble in a wet state.

3. The preparation method of claim 2, wherein the water is contained in an amount of 50 to 150 parts by weight based on 100 parts by weight of the first fine powder and the second fine powder.

4. The preparation method of claim 1, wherein the silica is contained in an amount of 0.005 to 0.5 parts by weight based on 100 parts by weight of the first fine powder and the second fine powder in the step of forming fine powder granules.

5. The preparation method of claim 1, wherein a moisture content of the first fine powder and the second fine powder is 40 to 60% in the step of forming fine powder granules.

6. The preparation method of claim 1, wherein the silica has a primary particle size of 5 to 100 nm.

7. The preparation method of claim 1, wherein the first fine powder and the second fine powder are mixed at a weight ratio of 10:1 to 1:1 in the step of forming fine powder granules.

8. The preparation method of claim 1, further comprising a step of drying the fine powder granules.

9. The preparation method of claim 8, further comprising a step of pulverizing or classifying the dried fine powder granules.

* * * * *